United States Patent [19]

Gemert

[11] Patent Number: 4,696,695

[45] Date of Patent: Sep. 29, 1987

[54] SULFAMOYL UREA DERIVATIVES

[75] Inventor: Barry V. Gemert, Massillon, Ohio

[73] Assignee: PPG Industries, Inc., Pittsburgh, Pa.

[21] Appl. No.: 892,989

[22] Filed: Aug. 4, 1986

Related U.S. Application Data

[60] Division of Ser. No. 791,269, Oct. 25, 1985, which is a continuation-in-part of Ser. No. 667,513, Nov. 1, 1984, abandoned.

[51] Int. Cl.$^4$ .................. C07D 239/69; A01N 43/54
[52] U.S. Cl. ...................................... 71/92; 544/332; 544/321
[58] Field of Search ............................ 544/332; 71/92; 544/321

[56] References Cited

U.S. PATENT DOCUMENTS 4,515,620  5/1985  Bohner ..................................... 71/91
4,559,081  12/1985  Van Gemert ........................... 71/93

FOREIGN PATENT DOCUMENTS 107624  5/1984  European Pat. Off. .

Primary Examiner—John M. Ford
Attorney, Agent, or Firm—Edward J. Whitfield

[57] ABSTRACT

The invention relates to herbicidally active sulfamoyl urea derivatives, including herbicidal formulations and uses thereof to control the growth of noxious plants, i.e., weeds.

4 Claims, No Drawings

SULFAMOYL UREA DERIVATIVES

CROSS REFERENCE TO RELATED APPLICATION

This is a division of application Ser. No. 791,269, filed Oct. 25, 1985, Pat. No. 4,622,065, which is a continuation-in-part of application Ser. No. 667,513 filed Nov. 1, 1984, since abandoned.

FIELD OF THE INVENTION

This invention relates to herbicidally active sulfamoyl urea derivatives, including herbicidal formulations uses thereof to control the growth of noxious plants, i.e., weeds.

DESCRIPTION OF THE INVENTION

This invention concerns sulfamoyl urea derivatives represented by the Formula I:

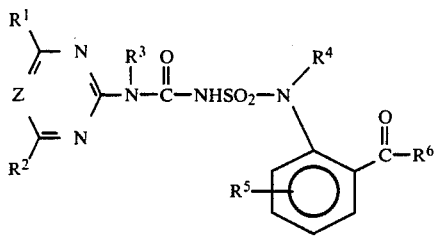

wherein:
Z is N or CH;
$R^1$ and $R^2$ are the same or different and represent halogen or $C_1$ to $C_6$ alkyl, substituted alkyl or alkoxy;
$R^3$ and $R^4$ are the same or different and represent hydrogen, $C_1$ to $C_4$ alkyl, alkoxyalkyl, haloalkyl, or up to $C_3$ alkenyl or alkynyl;
$R^5$ is hydrogen, halogen, or $C_1$ to $C_4$ alkyl or haloalkyl; and
$R^6$ is methyl or ethyl.

Preferred compounds within the scope of this invention are those wherein Z is nitrogen, $R^1$ is lower alkyl, e.g., methyl; $R^2$ is lower alkoxy, e.g., methoxy; $R^3$, $R^4$ and $R^5$ are hydrogen; and $R^6$ is methyl.

The Formula I compounds may conveniently be prepared in a two-step reaction, involving reacting in the first step a suitably substituted amino pyrimidine or amino triazine of the Formula II:

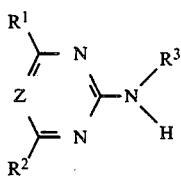

wherein $R^1$, $R^2$, $R^3$ and Z are as previously defined, with a halosulfonyl isocyanate of the formula OCN-SO$_2$-Hal, wherein Hal is halogen, e.g., chlorine, fluorine or bromine to form the corresponding halosulfonyl urea of the Formula III:

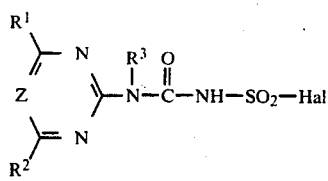

In the second step, the Formula III compound is reacted, preferably in the presence of an acid acceptor, e.g. triethylamine, with east a stoichiometric amount of a suitably substituted amine of the Formula IV:

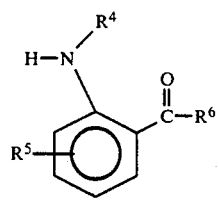

wherein $R^4$, $R^5$ and $R^6$ are as previously defined, to form a Formula I compound of the invention.

The invention is further illustrated by the following Examples which describe preparation of certain compounds of this invention.

The following Examples are illustrative of the preparation of certain preferred compounds of this invention.

EXAMPLE I

Preparation of:
1-(2-methylcarbonylphenylsulfamoyl)-3-(4-methyl-6-methoxy-1,3,5-triazin-2-yl)urea To a stirred solution of 0.01 mole of chlorosulfonyl isocyanate in methylene chloride maintained at 0°-5° C. via an ice bath was added 1.4 grams (0.01 mole) of 2-amino-4-methyl-6-methoxy-1,3,5-triazine. After two hours reaction time, a methylene chloride solution containing 1.35 grams (0.01 mole) of o-amino acetophenone and 1.0 gram (0.01 mole) of triethylamine is added dropwise. The reaction mixture was stirred rapidly while in the ice bath and was then removed and allowed to warm to room temperature. After standing overnight, the reaction mixture was poured into aqueous sodium carbonate. The aqueous layer was washed once with chloroform and filtered. Acidification with dilute aqueous hydrochloric acid resulted in a white precipitate which after suction filtration and vacuum drying afforded 2.4 grams of material confirmed by NMR analysis as the desired product.

EXAMPLE II

Preparation of:
1-(2-methylcarbonyl-4-fluorophenylsulfamoyl)-3-(4-methyl-6-methoxy-1,3,5-triazin-2-yl)urea To 75 milliliters of methylene chloride maintained at 0°-5° C. via an ice bath were added 1.4 grams of 4-methyl-6-methoxy-2-amino-1,3,5-triazine and 1.55 grams of chlorosulfonyl isocyanate. After stirring for 2 hours at ice bath temperature a methylene chloride solution containing 1.0 gram of triethylamine and 1.53 grams of 5-fluoro-2-amino-acetophenone was added dropwise. The stirred reaction mixture was permitted to warm to room temperature and was then shaken once with 2 percent aqueous hydrochloric acid then twice with water. Removal of solvent afforded a crystalline solid which was washed with a small amount of diethyl ether. Suction drying afforded light tan crystals identified by NMR analysis as the desired product.

EXAMPLE III

Preparation of:
1-(2-methylcarbonyl)-4-chlorophenylsulfamoyl)-3-(4-methyl-6-methoxy-1,3,5-triazin-2-yl)urea To 75 milliliters of methylene chloride maintained at 0°–5° C. via an ice bath were added 1.4 grams of 4-methyl-6-methoxy-2-amino-1,3,5-triazine and 1.55 grams of chlorosulfonyl isocyanate. After stirring for 2 hours at ice bath temperature a methylene chloride solution containing 1.0 gram of triethylamine and 1.7 grams of 5-chloro-2-aminoacetophenone was added dropwise. The stirred reaction mixture was permitted to warm to room temperature and was then shaken with cold, dilute aqueous hydrochloric acid solution. After phase separation, the organic layer was drawn-off, washed with water and evaporated affording a brown pasty residue. The residue was dissolved in 5 milliliters of methylene chloride. Diethyl ether was added and precipitation was initiated by scratching the flask. The crystalline precipitate was isolated by filtration, washed with diethyl ether and suction dried, affording 2.8 grams of white crystals confirmed by NMR analysis to be the desired product.

Although the invention has been illustrated by the foregoing Examples with regard to the preparation of certain compounds within the scope of Formula I, it is to be understood that other compounds within the scope of Formula I may readily be prepared by those skilled in the art simply by varying the choice of starting materials and using the same or similar techniques.

Weed control in accordance with this invention is effected by applying to the soil prior to emergence of weeds therefrom or to the plant surfaces subsequent to emergence from the soil, a herbicidally effective amount of a compound of this invention. It is, of course, to be understood that the term "a compound of this invention" also includes mixtures of such compounds or a formulation containing a compound or mixture of compounds of this invention.

The term "herbicidally effective amount" is that amount of a compound of this invention required to so injure or damage weeds such that the weeds are incapable of recovering following application while not causing substantial injury to any valuable crop amongst which the weeds might be growing. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as one or less pound per acre of a compound of this invention would be expected to provide satisfactory weed control, although in some instances application rates in excess of one pound per acre, e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.1 to 2.0 pounds per acre.

Of course, a compound of this invention can be formulated according to routine methods with any of several known and commonly used herbicidal diluents, adjuvants and carriers. The formulations can contain liquid carriers and adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America,* may be used in combination with a compound or compounds of the invention. Typically such formulations will contain from about 5 to about 95 percent by weight of a compound of this invention.

The herbicidal formulations contemplated herein can be applied by any of several method known to the art. Generally, the formulation will be surfaced applied as an aqueous spray. Such application can be carried out by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention are believed effective for preemergence or postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curly dock, field chickweed, dandelion, Russian knapweed aster, horsetail, ironweed, sesbania, cattail, wintercress, horsenettle, nutsedge, milkweed, sicklepod, and the like.

The compounds prepared as described in the Examples were individually screened for herbicidal efficacy, against a variety of broadleaf and grassy weed species, under controlled laboratory conditions of light, humidity and temperature. Solvent solutions of said compounds were applied, both preemergence and postemergence, to test flats containing the various weed species, and herbicidal efficacy was determined by periodic visual inspection, after application of the compounds. Herbicidal efficacy was determined on a Numerical Injury Rating (NIR) scale of from 0 (no injury) to 10 (all plants dead). A NIR rating of 7–9 indicates severe injury; a NIR rating of 4–6 indicates moderate injury, i.e., plant growth is reduced to the extent that normal growth would be expected only under ideal conditions; and a NIR rating of 1–3 indicates slight injury.

For example, the following table gives the average preemergence and/or postemergence NIR determined for each of the compounds prepared as described in Examples I through III on the broadleaf (BL) and grassy (GR) weed species to which the compounds were applied. Each compound was applied at the indicated rate of application in pounds per acre and the NIR was determined three weeks subsequent to application.

|  | I | II | III |
|---|---|---|---|
| Pre-BL | 9.0 | 6.3 | 8.3 |
| Pre-GR | 9.0 | 9.0 | 8.2 |
| Post-BL | 6.6 | 7.2 | 6.7 |
| Post-GR | 8.2 | 3.0 | 3.3 |
| Rate | 0.5 | 2 | 2 |

The broadleaf weeds used in the screening tests were coffeeweed, jimsonweed, tall morningglory, wild mustard, teaweed and velvetleaf. The grassy weeds used in the screening tests were barnyardgrass, large crabgrass, Johnsongrass, wild oats and yellow foxtail. In addition to the above observed herbicidal activities the compounds were found very effective, especially when applied preemergence, in controlling yellow nutsedge, a very difficult weed to control.

Although the invention has been described in considerable detail by the foregoing, it is to be understood that many variations may be made therein by those skilled in the art without departing from the spirit and scope thereof as defined by the appended claims.

I claim:

1. A compound represented by the formula:

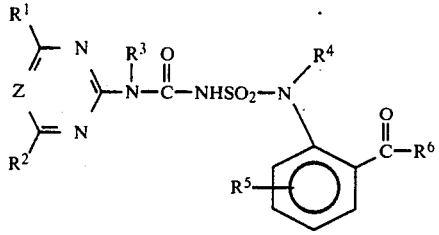

wherein:
Z is CH;
$R^1$ and $R^2$ are the same or different and represent halogen or $C_1$ to $C_6$ alkyl, or alkoxy;
$R^3$ and $R^4$ are the same or different and represent hydrogen, $C_1$ to $C_4$ alkyl, alkoxyalkyl, haloalkyl, or up to $C_3$ alkenyl or alkynyl;
$R^5$ is hydrogen, halogen or $C_1$ to $C_4$ alkyl or haloalkyl; and
$R^6$ is methyl or ethyl.

2. A compound of claim 1 wherein $R^1$ is lower alkyl, $R^2$ is lower alkoxy, $R^3$ $R^4$ and $R^5$ are hydrogen and $R^6$ is methyl.

3. A herbicidal formulation containing an agronomically acceptable carrier and a compound or mixture of compounds defined in claim 1.

4. In a method of controlling weeds wherein a herbicidally effective amount of herbicide is applied to a growth medium prior to emergence of weeds therefrom or to the weeds subsequent to their emergence from the growth medium, the improvement residing in using as the herbicide a compound or mixture of compounds defined in claim 1.

* * * * *